United States Patent [19]

Tse et al.

[11] Patent Number: 5,648,222

[45] Date of Patent: Jul. 15, 1997

[54] METHOD FOR PRESERVING CELLS, AND USES OF SAID METHOD

[75] Inventors: Doris B. Tse, Riverdale, N.Y.; Hui-Min Chung; Leonardus H. T. Van der Ploeg, both of Scotch Plains, N.J.

[73] Assignee: The Trustees of Columbia University in the City of New York, New York, N.Y.

[21] Appl. No.: 281,460

[22] Filed: Jul. 27, 1994

[51] Int. Cl.$^6$ ................................................ G01N 33/574
[52] U.S. Cl. .............. 435/7.23; 435/7.24; 435/7.25; 435/960; 435/962; 436/522; 436/519; 436/174; 436/176; 436/826; 436/64
[58] Field of Search ............................ 424/3, 11; 422/40; 435/1–1.3, 2, 7.1, 7.2, 7.21, 7.23, 7.24, 7.25, 960, 962; 436/501, 518, 522, 519, 538, 174, 176, 813, 826, 63, 64

[56] References Cited

U.S. PATENT DOCUMENTS

| | | | |
|---|---|---|---|
| 4,654,312 | 3/1987 | Chang et al. | 436/519 |
| 4,857,300 | 8/1989 | Maksem | 424/3 |
| 4,902,613 | 2/1990 | Chang et al. | 435/2 |
| 5,122,453 | 6/1992 | Martin et al. | 435/7.24 |
| 5,192,553 | 3/1993 | Boyse et al. | 424/529 |
| 5,348,741 | 9/1994 | Esposito et al. | 424/199.1 |

OTHER PUBLICATIONS

M. Ludgate et al, "T–Cell Subset Analysis of Cryopreserved Human Peripheral Blood Mononuclear Cells" in Immunology Letters 7:119–122 (1983).

D. Paterson et al, "Assessment of Oestrogen Receptor Content of Breast Carcinoma by Immunohistochemical Technique . . . " in J. Clin. Pathol. 43:46–51 (1990).

T. Takahashi et al, "Osmotic Stress and the Freeze–Thaw Cycle Cause Shedding of Fc and C3b Receptors . . . " in J. of Immunology, 134(6):4062–4068 (1985).

P. vanDam et al, "Comparative Evaluation of Fresh, Fixed, and Cryopreserved Solid Tumor Cells for Reliable Flow Cytometry . . . " in Cytometry 13:722–729 (1992).

H. Zola, Monoclonal Antibodies: A Manual of Techniques (CRC Press, Inc. Boca Raton, Florida 1987) pp. 112–115.

Bruch, J.F., et al. Trophoblast–Like Cells Sorted from Peripheral Maternal Blood Using Flow Cytometry: A Multiparametric Study Involving Transmission Electron Microscopy and Fetal DNA Amplification. Prenat. diagn. (1991) II: 787–798.

Cacheux, V., et al. Detection of 47XYY Trophoblast Fetal Cells in Maternal Blood by Fluorescence in situ Hybridization after Using Immunomagnetic Lymphocyte Depletion and Flow Cytometry Sorting. Fetal Diagn Ther (1992) 7: 190–194.

Covone, A.E., et al. Analysis of Peripheral Maternal Blood Samples for the Presence of Placenta–Derived Cells Using Y–Specific Probes and McAb H315. Prenat. diagn. (1988) 8: 591–607.

Psallidopoulos, M.C., et al. Integrated Proviral Human Immunodeficiency Virus Type 1 is Present in CD4+ Peripheral Blood Lymphocytes in Healthy Seropositive Individuals. Journal of Virology (1989) 63: 4626–4631.

Tse, D.B. and Pernis, B. Spontaneous Internalization of Class I Major Histocompatibility Complex Molecules in T Lymphoid Cells. J. Exp. Med. Jan. (1984) 159: 193–207.

Tse, D.B., et al. Intracellular Accumulation of T–Cell Receptor Complex Molecules in a Human T–Cell Line. Science (1986) 234: 748–751.

Primary Examiner—Carol A. Spiegel
Attorney, Agent, or Firm—John P. White

[57] ABSTRACT

This invention provides a method for preserving cells which comprises the steps of (a) suspending cells in a physiologically-acceptable, isotonic medium; and (b) fixing the cells so suspended at a temperature of less than about 10° C. under sufficiently hypertonic conditions so as to disperse the cells in a single, unagglutinated state, thereby preserving cells. This invention also provides a method for detecting cells separated from a sample which have been preserved according to the aforementioned method. This invention also provides a method for visualizing cells. Also provided is a method for detecting a metabolic process in cells present in a sample. This invention also provides a method for detecting the presence of rare cells in a sample which specifically possess on their surfaces a moiety recognized by a known ligand comprising preserving cells separated from the sample according to the aforementioned method for preserving cells. The subject invention also provides for quantitatively determining and isolating rare cells detected according to the afornmentioned method. Further provided are methods for determining whether a fetus is afflicted with a genetic abnormality, determining the gender of a fetus, determining whether a subject is afflicted with a tumor, and detecting in a subject the presence of cells expressing a malignant phenotype, each method comprising preserving cells according to the aforementioned method for preserving cells.

13 Claims, No Drawings

METHOD FOR PRESERVING CELLS, AND USES OF SAID METHOD

The invention disclosed herein was made with Government support under NIH Grant Nos. AI21784, GM14825, and CA39782 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Rare cells are often circulating in peripheral blood (1–5). For example, the frequency of circulating trophoblasts obtained from a subject carrying a 47, XYY fetus was approximately one in $10^5$ nucleated blood cells after pre-enrichment by gradient fractionation (5). The percentage of mononuclear cells infected with Human Immunodeficiency Virus (HIV) in the peripheral blood of HIV-infected subjects was 0.003–0.01% in asymptomatic subjects and 1–5% in subjects displaying symptoms associated with advanced stages of the disease (6–9). However, a technique for preserving cells obtained from biological specimens so that rare cells can be analyzed or isolated at a later time has not heretofore been disclosed.

Rare cells are a potential source for early detection or diagnosis of infection, malignancy, or genetic disorder. A technique for preserving cells obtained from biological specimens in a single, unagglutinated state would provide a means for such sensitive diagnosis. A single sample obtained from a subject containing cells which are preserved in a single, unagglutinated state may be analyzed multiple times, varying the parameters of analysis each time as desired yet avoiding the necessity of repeatedly obtaining samples from the same subject. Furthermore, preserved cells from different subjects may be more efficiently analyzed than cells from different subjects maintained in a viable state. Cells from a single subject obtained at different times or stages during the course of a disease may likewise be analyzed in a single, unagglutinated state at one time.

SUMMARY OF THE INVENTION

This invention provides a method for preserving cells which comprises the steps of (a) suspending cells in a physiologically-acceptable, isotonic medium; and (b) fixing the cells so suspended at a temperature of less than about 10° C. under sufficiently hypertonic conditions so as to disperse the cells in a single, unagglutinated state, thereby preserving the cells.

This invention also provides a method for detecting cells present in a sample which comprises the steps of (a) separating cells from the sample; (b) preserving the cells so separated according to the above-described method; and (c) detecting cells preserved in step (b), so as to thereby detect cells present in the sample.

This invention also provides a method for visualizing cells present in a sample which comprises the steps of (a) separating cells from the sample; (b) preserving the cells so separated according to the above-described method; and (c) visualizing the cells preserved in step (b) so as to thereby visualize cells present in the sample.

This invention also provides a method for detecting a metabolic process in cells present in a sample which comprises the steps of (a) separating cells from the sample; (b) contacting the cells so separated with a detectable substance capable of interacting with a metabolic substance in the pathway of the metabolic process; (c) collecting cells resulting from step (b) at a plurality of suitably spaced points in time; (d) preserving the cells so collected at each time point according to the above-described method of preserving cells; (e) detecting the presence of the detectable substance in the cells so preserved at each time point; and (f) determining the existence of a change in the presence of the detectable substance so detected, the existence of the change known to result from the metabolic process, so as to thereby detect the metabolic process in the cells present in the sample.

This invention also provides a method for detecting the presence of rare cells in a sample which cells specifically possess on their surfaces a moiety recognized by a known ligand which comprises the steps of (a) separating cells from the sample; (b) contacting the cells so separated with a known ligand, said ligand being detectable, under conditions which would permit the known ligand to specifically form a complex with the moiety recognized thereby, so as to thereby label cells possessing the moiety on their surfaces if present in the sample; (c) removing remaining uncomplexed ligand; (d) preserving the resulting cells according to the method of preserving cells described above so as to thereby preserve any cells labeled in step (b); and (e) detecting the presence of any labelled cells so preserved so as to thereby detect the presence of rare cells in the sample which specifically possess on their surfaces the moiety recognized by the known ligand.

Also provided is a method which comprises quantitatively determining cells detected according to the above-described method for detecting rare cells present in a sample, as well as a method which comprises isolating cells detected according to the above-described method.

This invention further provides a method for determining whether a fetus is afflicted with a genetic abnormality which comprises the steps of (a) obtaining a sample comprising fetal cells from the fetus, which sample comprises fetal cells which specifically possess on their surfaces a moiety recognized by a known ligand; (b) detecting the presence of fetal cells in the sample so obtained according to the above-described method for detecting rare cells present in a sample; and (c) determining whether the fetal cells so detected are characteristic of cells from a fetus having the genetic abnormality, so as to thereby determine whether the fetus is afflicted with the genetic abnormality.

This invention also provides a method for determining the gender of a fetus which comprises the steps of (a) obtaining a sample comprising fetal cells from the fetus, which sample comprises fetal cells which specifically possess on their surfaces a moiety recognized by a known ligand; (b) detecting the presence of fetal cells in the sample so obtained according to the above-described method for detecting the presence of rare cells in a sample; and (c) determining whether the fetal cells so detected possess two X chromosomes or an X chromosome and a Y chromosome, so as to thereby determine the gender of the fetus.

Also provided by the subject invention is a method of determining whether a subject is afflicted with a tumor normally tending to shed cells into the blood of a subject afflicted therewith which comprises the steps of (a) obtaining a blood sample from the subject; (b) removing erythrocytes from the blood sample so obtained; and (c) detecting the presence of tumor cells in the resulting sample according to the above-described method for detecting the presence of rare cells in a sample, so as to thereby determine whether the subject is afflicted with said tumor.

This invention further provides a method of detecting in a subject the presence of cells expressing a malignant phenotype which comprises the steps of (a) obtaining a suitable sample from the subject; (b) removing erythrocytes from the sample so obtained; and (c) detecting the presence of cells expressing the malignant phenotype in the resulting sample according to the above-described method of detecting the presence of rare cells in a sample, so as to thereby detect in the subject the presence of cells expressing the malignant phenotype.

This invention also provides a method for determining whether a subject who has been treated with an anti-tumor therapy, said therapy having included chemotherapy, possesses cells expressing a malignant phenotype which have undergone a genetic alteration associated with drug resistance, which comprises the steps of (a) detecting in the subject the presence of cells expressing a malignant phenotype according to the above-described method and; (b) determining whether any cells so detected are characteristic of cells which have undergone a genetic alteration associated with drug resistance, thereby determining whether the subject possesses cells expressing a malignant phenotype which have undergone a genetic alteration associated with drug resistance.

DETAILED DESCRIPTION OF THE INVENTION

This invention provides a method for preserving cells which comprises the steps of (a) suspending cells in a physiologically-acceptable, isotonic medium; and (b) fixing the cells so suspended at a temperature of less than about 10° C. under sufficiently hypertonic conditions so as to disperse the cells in a single, unagglutinated state, thereby preserving the cells.

The method of the subject invention may further comprise a step of separating cells from a cell-containing sample. Examples of cell-containing samples are well-known in the art and include, but are not limited to, biological specimens such as biopsies, tissue aspirates, lavages, blood samples including both specific and peripheral blood samples, semen, and urine. Suitable conditions for separating cells from a cell-containing sample are any conditions or procedures known to those of ordinary skill in the art for removing all or most of the extracellular material in a cell-containing sample from the cells in the sample. Such procedures are well-known in the art and include, but are not limited to, grinding and sieving to remove particulate matter from a sample, digesting any extracellular matrix in a sample, and centrifuging to remove extracellular fluid from a sample. Preferably, the cells are separated from the cell-containing sample at a temperature of from about 0° C. to about 10° C.

If the cells separated from a sample include erythrocytes, unless preservation of the erythrocytes is desired, the erythrocytes are preferably removed after separation of the cells from the extracellular material. Any method for removing erythrocytes known in the art may be used in the subject invention, so long as the cells to be preserved remain viable until they are contacted with the fixative used for fixing the cells. For example, the erythrocytes may be removed by centrifugation through a density gradient. Alternatively, the erythrocytes may be lysed and the nucleated cells recovered after centrifugation. Methods for lysing erythrocytes are known to those of ordinary skill in the art and include contacting the erythrocytes with a known lysing reagent. If a known lysing reagent is used, the lysing reagent is preferably attenuated with serum so as to be physiologically compatible with the nucleated cells to be preserved. Also preferred as a lysing reagent is ammonium chloride. In one embodiment, the lysis occurs at a temperature of from about 0° C. to about 10° C. In another embodiment, the lysis occurs at a temperature of from 0° C. to about 4° C. In the preferred embodiment, the lysis occurs at a temperature of about 4° C.

As used herein, the term "physiologically-acceptable, isotonic medium" means any medium in which cells remain viable. Such media are well known to those of ordinary skill in the art and include phosphate-based buffers; bicarbonate-based buffers; and citrate-based buffers. For certain applications of the method of the subject invention, preservation of the protein moieties of the cells may be especially desired, for example where antigens on the surfaces of the cells are to be used for later immunodetection of the preserved cells. For such applications, a phosphate-based buffer is preferred as the physiologically-acceptable, isotonic medium. For other applications of the method of the subject invention, preservation of the nucleic acid moieties of the cells may be especially desired, for example where the DNA in the cells is to be hybridized with a nucleic acid probe. For these applications, a citrate-based buffer is preferred as the physiologically-acceptable, isotonic medium. An isotonic medium is any medium which contains a concentration of solutes substantially identical to the concentration of solutes inside a cell, i.e. a medium of about 0.3 molarity.

The pH of physiologically-acceptable media are any pH in which cells remain viable. pH at which cells remain viable are known to those of ordinary skill in the art and are typically between about 5.5 and about 8.0. A pH of about 7.4 is preferred.

In one embodiment, the cells are suspended in the physiologically-acceptable, isotonic medium at a temperature of from about 0° C. to about 10° C. In another embodiment, the cells are suspended at a temperature of from about 0° C. to about 4° C.. In another embodiment, the cells are suspended at a temperature of about 4° C.

After the cells are suspended in the physiologically-acceptable, isotonic medium, they are fixed at a suitable temperature and under sufficiently hypertonic conditions so as to disperse the cells in a single, unagglutinated state. In the subject invention, the cells may be fixed by contacting them with a fixative for a sufficient period of time. As used herein, the term "fixing" means treating cells so as to preserve some structural aspect of the cells, for example the size, organization, protein moieties, and/or nucleic acid moieties of the cells.

By fixing cells at a suitable temperature and under sufficiently hypertonic condition so as to disperse the cells in a single, unagglutinated state, the individual cells may be analyzed or observed without obstruction from one another either immediately or many months or even years after they have been preserved.

Any fixative may be used in the above described method, provided the fixative fixes the cells gradually enough so that the cells are fixed while the temperature and hypertonicity of the suspension are such that the cells are dispersed in a single, unagglutinated state. Preferably, the fixative is formaldehyde.

If the fixative is formaldehyde, the final concentration of formaldehyde in the solution in which the cells are fixed should be such that the cells are fixed at a suitable temperature and while the solution is sufficiently hypertonic so that the cells are dispersed in a single, unagglutinated state. Preferably, the final formaldehyde concentration is between 0.5% and 2%. Therefore, the concentration of formaldehyde groups in the solution contacting the cells should be sufficient to achieve a final formaldehyde concentration in the solution in which the cells are fixed within the aforementioned range. Formaldehyde solutions useful in the method of the subject invention and having a suitable aldehyde concentration are readily available to those of ordinary skill in the art. For example, formalin (approximately 37% formaldehyde in methanol) may be used to fix the cells in the method of the subject invention. Alternatively, paraformaldehyde may be dissolved to form a solution of short chain polymers and monomers of formaldehyde, for example by heating paraformaldehyde in an appropriate solvent and/or by increasing the pH of paraformaldehyde dispersed in an appropriate solvent. Appropriate solvents for dissolving formaldehyde are well known to those of ordinary skill in the art. The concentration of formaldehyde in the formaldehyde solution to be added to the cell suspension may be ascertained by means well known in the art, for example by adding Schiff's reagent to the formaldehyde solution and spectrophotometrically determining the aldehyde concentration as a function of the color of the solution resulting therefrom.

For purposes of this invention, the temperature at which the cells are fixed is less than about 10° C.. In one embodiment, the temperature is from about 0° C. to about 10° C. In another embodiment, the temperature is from about 0° C. to about 4° C. In the preferred embodiment, the temperature is about 4° C. Without limiting the scope of the subject invention, it is hypothesized that such temperatures help disperse cells in a single, unagglutinated state by preventing the polymerization of microtubules in the cells and thereby causing the cells in the sample to "round-up", i.e. separate from one another.

In the method of the subject invention, the cells are fixed under sufficiently hypertonic conditions such that, given the particular temperature of the suspension, the cells are dispersed in a single, unagglutinated state. As used herein, the term "hypertonic" means having a concentration of solutes in a solution which concentration is greater than the concentration of solutes inside a cell, i.e. a concentration greater than about 0.3 molarity. By suspending the cells in a hypertonic solution, the cells are separated from one another, thus helping to prevent the cells from agglutinating. Any solutes for making a solution hypertonic may be used in the subject invention. For example glucose or sucrose may be dissolved in the solution in which the cells are fixed. In one embodiment, the solution in which the cells are fixed is rendered hypertonic solely via the dissolved fixative, for example via the dissolved formaldehyde in a formaldehyde solution. A final concentration of formaldehyde in the isotonic medium in which the cells are suspended of between about 0.5% to about 2% is adequate to render the solution hypertonic to preserve cells in a single, unagglutinated state when the temperature is less than about 10° C.

Optionally, chemicals may be added to the fixative prior to contacting the cells with the fixative in order to render the cells permeable to ligands which bind to intracellular moieties. Binding of ligands to intracellular moieties may be desired for purposes of visualizing, detecting, or isolating the cells after they have been preserved. Chemicals which increase the permeability of cells are well known in the art. The organic solvent acetone is preferred as a chemical for increasing the permeability of cells when preservation of protein moieties is desired. The organic solvent methanol is preferred as a chemical for increasing the permeability of cells when preservation of nucleic acid moieties is desired. The organic solvent ethanol is another chemical known in the art to increase the permeability of cells.

Alternatively, the cells may be suspended in a solution of formaldehyde combined with lysine, sucrose, and periodate for fixation of both protein moieties and nucleic acid moieties, or when the cells are to be studied by electron microscopy. A detergent may then be added to the solution in which the cells are fixed to permeabilize the plasma membrane and the nuclear envelope of the cells.

Preferably, when chemicals which are organic solvents are added to permeabilize the cells, they are added so that their combined final concentration in the solution in which the cells are fixed is between about 0.3% and about 60%. The greater the final concentration of organic solvent in the cell suspension, the greater the permeability obtained.

The time elapsing before the cells are fixed once the fixative has been added in the method of the subject invention depends on the final concentration of the fixative in the cell suspension in which the cells are fixed. The greater the final fixative concentration in the cell suspension, the shorter the time elapsing before the cells in the suspension are fixed. For example, if the cell suspension contains a final formaldehyde concentration of about 1%, the cells in the suspension are fixed in approximately thirty minutes. The temperature and the hypertonicity of the suspension must remain sufficient to maintain the cells dispersed in a single, unagglutinated state until the cells are fixed. However, once the cells are fixed, they may be stored indefinitely.

This invention also provides a method for detecting cells present in a sample which comprises the steps of (a) separating cells from the sample; (b) preserving the cells so separated according to the above-described method; and (c) detecting cells preserved in step (b), so as to thereby detect cells present in the sample.

Methods for separating cells from a sample are well-known in the art. Any method for separating cells can be used in the subject invention, including, but not limited to, the well-known methods for separating cells from a cell-containing sample discussed above.

In one embodiment, all of the cells preserved in step (b) are detected. In another embodiment, only cells possessing a unique phenotype preserved in step (b) are detected.

Methods for detecting cells are known in the art and any such method may be used in the method for detecting cells of the subject invention. Examples of methods known in the art for detecting cells include, but are not limited to, labelling cells with a fluorescent marker followed by analysis with a fluorescent activated cell sorter, and visualizing cells, for example as in histochemistry.

As used herein, detecting cells includes detecting any cells which remain after excluding cells possessing a unique phenotype. Cells possessing a unique phenotype may be excluded by contacting them with a detectable ligand which recognizes a moiety which the cells possessing the unique phenotype specifically express, thereby labelling cells possessing the unique phenotype, and subsequently excluding any cells so labelled.

Preservation of cells in a singe, unagglutinated state according to the method of the subject invention offers advantages for detecting cells. For example, fluorescently-labelled cells in a single, unagglutinated state may be more accurately detected by a fluorescence activated cell sorter than fluorescently-labelled cells which are partially agglutinated.

When the method for detecting cells is visualizing the cells, any method known in the art for visualizing cells may be used. Examples of methods known in the art for visualizing cells include, but are not limited to, light microscopy and phase-contrast microscopy.

Known visualization methods which may be employed in the subject invention may comprise staining cellular molecules and organelles with known staining reagents, such as eosin or methylene blue. Also, cellular molecules or organelles of interest may be visualized by tagging them with a visualizable marker such as a fluorescently labelled antibody or fluorescently labelled probe, as for example in fluorescence in situ hybridization. In the method of the subject invention, the tagging may occur either before or after the preservation step. Furthermore, the molecules or organelles may be either on the surface of the cells or in the interior of the cells.

The subject invention also provides a method for visualizing cells present in a sample which comprises the steps of (a) separating cells from the sample; (b) preserving the cells so separated according to the method of the subject invention; and (c) visualizing the cells preserved in step (b) so as to thereby visualize cells present in the sample.

Methods for visualizing cells are well-known in the art, and any such method may be used for visualizing the cells preserved in the method of the subject invention. Methods known in the art for visualizing cells are described above.

As discussed above, the method of the subject invention preserves the cells in a single, unagglutinated state. Therefore, the method of the subject invention offers a means for measuring or visualizing a detectable substance in cells at any particular point in time, the presence of which substance in the cells may change over time as a result of a cellular metabolic process. Accordingly, this invention also provides a method for detecting a metabolic process in cells present in a sample which comprises the steps of (a) separating cells from the sample; (b) contacting the cells so separated with a detectable substance capable of interacting with a metabolic substance in the pathway of the metabolic process; (c) collecting cells resulting from step (b) at a plurality of suitably spaced points in time; (d) preserving the cells so collected at each time point according to the method of the subject invention; (e) detecting the presence of the detectable substance in the cells so preserved at each time point; and (f) determining the existence of a change in the presence of the detectable substance so detected, the existence of the change known to result from the metabolic process, so as to thereby detect the metabolic process in the cells present in the sample.

Metabolic processes occurring in cells which may be detected according to the subject invention are well known in the art and include, but are not limited to, the metabolism of a drug in a cell or the internalization of a particular cell receptor. For example, the internalization of low density lipoprotein (LDL) receptors to which LDL has bound may be detected according to the subject invention. Detecting LDL receptor internalization would be useful, for example, for determining familial hypercholesterolemia.

As used herein, a "metabolic substance" is any substance which participates in or is produced by a metabolic process. In one embodiment, the metabolic substance is a metabolite of the metabolic process. In another embodiment, the metabolic substance is an intermediate of the metabolic process. In still another embodiment, the metabolic substance is a product of the metabolic process. In still another embodiment, the metabolic substance is a byproduct of the metabolic process.

As used herein, "the pathway of the metabolic process" indicates the series of interactions of those metabolic substances which make up the metabolic process. Such interactions include, but are not limited to, formations of complexes and chemical reactions.

Substances capable of interacting with a metabolic substance in the pathway of a metabolic process useful in the subject invention are well-known and are to be selected based upon the metabolic substance, which in turn is selected based upon the particular metabolic process to be detected. For example, if the metabolic process to be detected is the metabolism of a drug, the metabolic substance may be an enzyme capable of converting the drug to a product, and the substance capable of interacting with the enzyme may be the drug itself. As another example, if the metabolic process to be detected is the internalization of a particular cell receptor, the metabolic substance may be the cell receptor, and the substance interacting with the cell receptor a ligand which binds to the cell receptor or an antibody which specifically recognizes the cell receptor.

As used herein, substances capable of interacting with a metabolic substance include, but are not limited to, substances which are capable of forming a specific complex with the metabolic substance, as well as substances which are capable of reacting with the metabolic substance so as to form a distinct product.

In the method for detecting a metabolic process described above, the substance capable of interacting with the metabolic substance in the pathway of the metabolic process must be detectable. Detectable substances are well-known to those of ordinary skill in the art and include, but are not limited to, substances conjugated to a detectable marker, such as a fluorophore; enzymes which may convert a substrate into a chromogenic product; and molecules which are specifically recognized by a known antibody.

Changes in the presence of the detectable substance known to result from a particular metabolic process are ascertainable by means known to those of ordinary skill in the art. Such changes include, but are not limited to, changes in the location of the substance within the cell, or changes in the quantity of the substance.

Preservation of the cells in a single, unagglutinated state according to the method of the subject invention offers advantages for certain applications, such as for detecting or isolating rare cells. Accordingly, in one embodiment of the method of the subject invention, the cells preserved include rare cells. As used herein, the term "rare cells" means cells possessing a unique phenotype whose frequency in a sample is no greater than about 5% of the total cell population in said sample. In one embodiment, the frequency of the cells is not greater than about 1%. In another embodiment, the frequency is not greater than about 0.1%. In still another embodiment, the frequency is less than 0.0001%. Assume, for example, that cells possessing phenotype X constitute only about 0.0001% of the total number of cells in a sample, said sample being blood. Cells possessing the phenotype X are therefore rare cells for purposes of the subject invention.

Rare cells may be either nucleated or non-nucleated. Rare cells include, but are not limited to, the following cells found in certain blood samples: cells expressing a malignant phenotype; fetal cells, such as fetal cells in maternal peripheral blood; tumor cells, such as tumor cells which have shed from a tumor into an afflicted subject's blood; cells infected with a virus, such as cells infected with HIV; cells transfected with a gene of interest; and aberrant subtypes of T-cells or B-cells present in the peripheral blood of subjects afflicted with autoreactive disorders.

Rare cells possessing a particular phenotype include rare cells which specifically possess on their surfaces a moiety recognized by a known ligand. The moiety recognized by the known ligand may be complexed with the known ligand after the cells have been preserved according to the method of the subject invention. Alternatively, the moiety recognized by the known ligand may be complexed with the known ligand prior to preservation of the cells according to the method of the subject invention. Accordingly, this invention also provides a method for detecting the presence of rare cells in a sample which cells specifically possess on their surfaces a moiety recognized by a known ligand which comprises the steps of (a) separating cells from the sample; (b) contacting the cells so separated with the known ligand, said ligand being detectable, under conditions which would permit the known ligand to specifically form a complex with the moiety recognized thereby so as to thereby label cells possessing the moiety on their surfaces if present in the sample; (c) removing remaining uncomplexed ligand; (d) preserving the resulting cells according to the method of the subject invention so as to thereby preserve any cells labelled in step (b); and (e) detecting the presence of any labelled cells so preserved so as to thereby detect the presence of rare cells in the sample which specifically possess on their surfaces the moiety recognized by the known ligand.

Any method for separating cells from a sample may be used in the method described above, and such methods for separating cells from a sample are well-known in the art as described above.

In one embodiment of the method for detecting the presence of rare cells in a sample which specifically possess on their surfaces a moiety recognized by a known ligand, the rare cells which specifically possess on their surfaces a moiety recognized by a known ligand are nucleated cells. In different embodiments when the rare cells are nucleated cells, the rare cells are cells expressing a malignant phenotype, fetal cells, tumor cells, cells infected with a virus, or cells transfected with a gene of interest.

Nucleated cells which express a malignant phenotype and which specifically possess on their surfaces a moiety recognized by a known ligand include, but are not limited to, leukemia cells, the phenotype of which is the presence of the calla antigen on their cell surfaces.

Ligands which form a complex with moieties on the surfaces of cells which express a malignant phenotype are well known and may be obtained by means well known to those of ordinary skill in the art. For example, a ligand which recognizes a moiety on the surfaces of the cells expressing the malignant phenotype may be obtained by known immunological methods, such as by injecting a mammal with cells which possess on their surfaces the moiety and subsequently obtaining the antiserum from the mammal, or by forming hybridomas from the spleen cells of a mammal infected with cells which possess on their surfaces the moiety and subsequently obtaining monoclonal antibodies which recognize the moiety from the hybridomas. An example of a known ligand which recognizes a moiety on the surface of a cell expressing a malignant phenotype is the anti-calla antibody, which recognizes an epitope of the calla antigen.

Fetal cells which specifically possess on their surfaces a moiety recognized by a known ligand are well known in the art and include, but are not limited to, trophoblasts.

Ligands which recognize moieties which fetal cells specifically possess on their surfaces are well known and may be obtained using methods known in the art, for example the well-known immunological techniques for producing polyclonal and monoclonal antibodies described above. Examples of known antibodies which bind to epitopes which fetal cells specifically possess on their surfaces include, but are not limited to, the anti-trophoblast monoclonal antibodies FD066Q (10), FD046B (10), and PI 153/3 (ATCC No. TIB 198).

Tumor cells which specifically possess on their surfaces a moiety recognized by a known ligand are well known to those of ordinary skill in the art. In one embodiment, these tumor cells are tumor cells originating from a tumor normally tending to shed cells into the blood stream of a subject afflicted therewith. Such tumors include, for example, melanomas, breast tumors, spleen tumors, liver tumors, and kidney tumors.

Ligands which bind to moieties which tumor cells specifically possess on their surfaces are well known and may be obtained using methods well known to those of ordinary skill in the art, for example the well-known immunological techniques for producing antibodies described above. Ligands which bind to moieties which tumor cells specifically possess on their surfaces include, but are not limited to, the monoclonal antibodies D14 (ATCC No. HB 8439) and M111 (ATCC No. HB 8438), each of which recognize epitopes on the surfaces of melanomas, and the monoclonal antibody 317G5 (ATCC No. HB 8485) which recognizes an epitope on the surfaces of cells from breast tumors.

Cells which are infected with a virus and specifically possess on their surfaces moieties unique to the virus and recognized by a known ligand are well known to those of ordinary skill in the art. Examples of cells infected with a virus which specifically possess on their surfaces a moiety recognized by a known ligand include, but are not limited to, cells infected with Human Immunodeficiency Virus (HIV) which, for example, express on their surfaces as a moiety the HIV viral envelope protein and therefore specifically possess epitopes on their surfaces unique to the HIV viral envelope protein.

Ligands which recognize moieties which cells infected with a virus specifically possess on their surfaces are well known and may be obtained using methods well known to those of ordinary skill in the art, for example the immunological methods for producing antibodies discussed above. Examples of ligands which recognize moieties specifically on the surfaces of cells infected with a virus include, but are not limited to, the anti-gp120 antibody 0.5 β (NIH AIDS Reference Reagent No. 904), which recognizes the HIV viral envelope protein specifically on the surfaces of HIV infected cells. Further examples of ligands which recognize moieties specifically on the surfaces of cells infected with a virus include the monoclonal antibody designated 0.5 α (ATCC No. HB 8755). The 0.5 α antibody recognizes an epitope specifically present on the surfaces of cells infected with Human T-cell Leukemia Virus type 1 (HTLV-1).

Cells transfected with a gene of interest which specifically possess on their surfaces a moiety recognized by a known ligand are well known in the art. As used herein, the phrase "gene of interest" means a gene which may be transfected into a cell. An example of a gene of interest is a gene encoding a receptor, such as the T cell CD4 receptor. The subject method for detecting cells transfected with a gene of interest would be useful, for example, for detecting cells transfected with a gene encoding a putative receptor in a sample comprising cells transfected with a genetic library, by contacting the sample with a known ligand to the putative receptor.

When the rare cells which specifically possess on their surfaces a moiety recognized by a known ligand to be detected according to the subject method are nucleated cells, the method of the subject invention preferably comprises removing any erythrocytes prior to preserving the cells. Any method for removing erythrocytes known to those of ordinary skill may be used to remove erythrocytes in the method of the subject invention. Methods for removing erythrocytes are well known in the art as described above. If a known lysing reagent is used in the process of removing the erythrocytes, the lysing reagent is preferably attenuated with serum so as to be physiologically compatible with the nucleated cells to be preserved. Also preferred as a lysing reagent is ammonium chloride. In one embodiment, the lysis occurs at a temperature of from about 0° C. to about 10° C. In another embodiment, the lysis occurs at a temperature of from 0° C. to about 4° C. In another embodiment, the lysis occurs at a temperature of about 4° C. After lysis, the nucleated cells may be recovered, for example, by centrifugation.

In one embodiment of the subject method for detecting rare cells which specifically possess on their surfaces a moiety recognized by a known ligand, the moiety is a receptor. In another embodiment, the moiety is an epitope and the known ligand is an antibody which binds to the epitope. Receptors and epitopes specifically on the surfaces of cells and the ligands recognizing them are well known in the art and include, but are not limited to, the receptors, epitopes and ligands described above.

In the subject method for detecting rare cells which specifically possess on their surfaces a moiety recognized by a known ligand, the known ligand must be a detectable ligand. Detectable ligands are known to those of ordinary skill in the art and include, but are not limited to, radiolabeled substances; iron-binding substances such as ferritin; magnetically charged substances; ligands conjugated to a detectable marker, such as an enzyme capable of generating a chromogenic product, or a fluorescent dye such as fluorescein; or ligands permitting detection through contact with a second detectable ligand. Any detectable ligand known in the art may be used in the subject invention and may be selected based on the anticipated application for the preserved cells. If the detectable ligand is a ligand conjugated to a detectable marker, the ligand is conjugated to the detectable marker before the cells are contacted with the ligand. If the detectable ligand is a ligand permitting detection through contact with a second detectable ligand, in one embodiment the ligand is contacted with the second detectable ligand before the cells are contacted with the ligand. In another embodiment, the ligand is contacted with the second detectable ligand after the cells are contacted with the ligand but before the cells are preserved. In still another embodiment, the ligand is contacted with the second detectable ligand after the cells in the sample are preserved.

Conditions permitting the known ligand to specifically form a complex with the moiety recognized thereby are well known in the art. In one embodiment, the cells are contacted with the known ligand at a temperature of from about 0° C. to about 10° C. In another embodiment, the cells are contacted with the known ligand at a temperature of from about 0° C. to about 4° C. In another embodiment, the cells are contacted with the known ligand at a temperature of about 4° C. In still another embodiment, the cells are contacted with the known ligand at a temperature which is physiologically compatible with the cells, for example a temperature of about 37° C.

Any method for detecting the presence of labelled cells known in the art may be used in the subject method for detecting the presence of rare cells in a sample which specifically possess on their surfaces a moiety recognized by a known ligand. The method for detecting the presence of labelled cells may be chosen based on the particular type of detectable ligand used. Examples of methods for detecting labelled cells which may be used in the subject method include, but are not limited to, immunoaffinity chromatography when the detectable ligand is an antibody, separation by magnetic beads when the detectable ligand is a magnetically charged substance, and fluorescence activated cell sorting when the detectable ligand is conjugated to a fluorophore. A further example of a method for detecting labelled cells which may be used in the subject method is visualization by light microscopy.

The above-described method for detecting rare cells present in a sample may further comprise quantitatively determining any labelled cells detected in step (e). Any method for quantitatively determining cells may be used in the subject method. Methods for quantitatively determining cells are well-known to those of ordinary skill in the art and include, but are not limited to, counting cells with a fluorescence activated cell sorter as well as using immunoturbidity assays.

The above-described method for detecting rare cells present in a sample may further comprise isolating any labelled cells detected in step (e). Any method for isolating labelled cells known in the art may be used in the subject method. The method for isolating labelled cells may be chosen based on the particular type of detectable ligand used. Examples of methods for isolating cells which may be used in the subject method include, but are not limited to, immunoaffinity chromatography when the detectable ligand is an antibody, separation by magnetic beads when the detectable ligand is a magnetically charged substance, and fluorescence activated cell sorting when the detectable ligand is conjugated to a fluorophore.

In another embodiment of the above-described method for detecting the presence of rare cells present in a sample, the method further comprises isolating any cells which are not detected in step (e). Isolation of cells which are not detected in step (e) may be accomplished by excluding the labelled cells detected in step (e). The method for excluding labelled cells may be chosen based on the particular type of detectable ligand used. Examples of methods for excluding labelled cells which may be used in the subject method include, but are not limited to, immunoaffinity chromatography when the detectable ligand is an antibody, separation by magnetic beads when the detectable ligand is a magnetically charged substance, and fluorescence activated cell sorting when the detectable ligand is conjugated to a fluorophore.

This invention further provides a method for determining whether a fetus is afflicted with a genetic abnormality which comprises the steps of (a) obtaining a sample comprising fetal cells from the fetus, which sample comprises fetal cells which specifically possess on their surfaces a moiety recognized by a known ligand; (b) detecting the presence of fetal cells in the sample so obtained according to the method for detecting the presence of rare cells in a sample described above; and (c) determining whether the fetal cells so detected are characteristic of cells from a fetus having the genetic abnormality, so as to thereby determine whether the fetus is afflicted with the genetic abnormality.

Any method for obtaining a sample comprising fetal cells from a fetus may be used in the subject invention, and such methods are well-known in the art. Methods for obtaining a sample comprising fetal cells from a fetus well-known in the art include, but are not limited to, withdrawing a sample of peripheral blood from the mother bearing the fetus.

Any method for determining whether fetal cells are characteristic of cells from a fetus possessing a genetic abnormality may be used in the subject method. Such methods are well-known to those of ordinary skill in the art. For example, fetal cells characteristic of cells from a fetus having Down syndrome may be determined by contacting the preserved fetal cells with a fluorescently-labeled nucleic acid probe specific for chromosome 21 and visualizing the cells by fluorescence in situ hybridization. The presence of three chromosome 21-specific signals indicates the fetus has Down syndrome. As another example, fetal cells characteristic of cells from a fetus having Turner syndrome may be determined by contacting the preserved fetal cells with a fluorescently-labeled X-chromosome specific nucleic acid probe and a fluorescently-labeled Y-chromosome specific nucleic acid probe, followed by visualizing the cells by fluorescence in situ hybridization. The presence of a single X-chromosome (with no Y-chromosome) indicates the fetus has Turner syndrome.

In one embodiment of the subject method for determining whether a fetus is afflicted with a genetic abnormality, the fetal cells detected in step (b) are isolated prior to determining whether they are characteristic of cells from a fetus having the genetic abnormality in step (c). Any method for isolating cells may be used and will be selected based on the particular detectable ligand used in the method for detecting fetal cells in step (b). Such methods for isolating cells are well-known to those of ordinary skill in the art as discussed above.

This invention also provides a method for determining the gender of a fetus which comprises the steps of (a) obtaining a sample comprising fetal cells from the fetus, which sample comprises fetal cells which specifically possess on their surfaces a moiety recognized by a known ligand; (b) detecting the presence of fetal cells in the sample so obtained according to the method for detecting the presence of rare cells in a sample described above; and (c) determining whether the preserved, labelled, fetal cells in the sample so obtained possess two X chromosomes or an X and a Y chromosome, so as to thereby determine the gender of the fetus.

Any method for determining whether fetal cells possess two X chromosomes or an X and a Y chromosome may be used in the subject method. Such methods are well-known to those of ordinary skill in the art and include, but are not limited to, contacting cells with a detectable nucleic acid probe specific for a DNA sequence present only on an X chromosome and a detectable nucleic acid probe specific for a DNA sequence only on a Y chromosome under conditions suitable to permit hybridization of the probes to the DNA sequences if present within the nuclei of the cells and subsequently detecting the presence of any hybridized probes. The presence of two X chromosomes indicates the fetus is a normal female. The presence of an X and a Y chromosome indicates that the fetus is a normal male.

In one embodiment of the subject method for determining the gender of a fetus, the fetal cells detected in step (b) are isolated prior to determining whether they possess two X chromosomes or an X and a Y chromosome in step (c). Any method for isolating cells may be used and will be selected based on the particular detectable ligand used in the method for detecting fetal cells in step (b). Such methods for isolating cells are well-known to those of ordinary skill in the art as discussed above.

Also provided is a method of determining whether a subject is afflicted with a tumor normally tending to shed cells into the blood of a subject afflicted therewith which comprises the steps of (a) obtaining a blood sample from the subject; (b) removing erythrocytes from the blood sample so obtained; and (c) detecting the presence of tumor cells in the resulting sample according to the method for detecting the presence of rare cells in a sample which specifically possess on their surfaces a moiety recognized by a known ligand described above, so as to thereby determine whether the subject is afflicted with said tumor.

Tumors normally tending to shed cells into the blood of a subject afflicted therewith are well-known in the art as described above and include, but are not limited to, melanomas, breast tumors, spleen tumors, liver tumors, and kidney tumors.

Any method for obtaining a blood sample from a subject may be used in the subject method, and such methods are well-known to those of ordinary skill in the art.

Any method for removing erythrocytes from a blood sample may be used in the subject method, and such methods are well-known to those of ordinary skill in the art as described above.

This invention further provides a method of detecting in a subject the presence of cells expressing a malignant phenotype which comprises the steps of (a) obtaining a suitable sample from the subject; (b) removing erythrocytes from the sample so obtained; and (c) detecting the presence of cells expressing the malignant phenotype in the resulting sample according to the method for detecting the presence of rare cells in a sample which specifically possess on their surfaces a moiety recognized by a known ligand described above, so as to thereby detect in the subject the presence of cells expressing the malignant phenotype.

Cells expressing a malignant phenotype are well-known in the art as described above. As used herein, a "suitable sample" is a sample in which cells expressing a malignant phenotype would be expected in an afflicted subject. Such samples are well-known in the art and include, but are not limited to, biopsies, tissue aspirates, lavages, and biological fluid samples such as blood or urine. Any method for removing erythrocytes from a sample may be used in the subject method.

In one embodiment, the suitable sample is obtained from a subject afflicted with a tumor. In another embodiment, the suitable sample is obtained from a subject previously afflicted with a tumor which tumor has been removed. In a further embodiment, the suitable sample is obtained from a subject who has been treated with an anti-tumor therapy such as radiotherapy or chemotherapy.

When the suitable sample is obtained from a subject previously afflicted with a tumor which tumor has been removed and characterized as benign or quiescent, the subject method for detecting in a subject the presence of cells expressing a malignant phenotype is useful, for example, for monitoring the transition of tumor cells remaining in the subject from a benign or quiescent phenotype to a malignant or aggressive phenotype.

When the suitable sample is obtained from a subject who has been treated with an anti-tumor therapy, cells expressing a malignant phenotype detected according to the subject method may be further analyzed to determine whether they possess a genetic alteration associated with the anti-tumor therapy. Anti-tumor therapies resulting in genetic alterations in cells expressing a malignant phenotype which may be determined according to the subject invention include any anti-tumor therapy known to those of ordinary skill in the art. Anti-tumor therapies known in the art include, but are not limited to, radiotherapy and chemotherapy.

Genetic alterations associated with radiotherapy include mutations which are known to increase sensitivity to radiation in cells. Accordingly, the method of the subject invention is useful, for example, for assessing whether radiotherapy will be cytotoxic to cells having a malignant phenotype in an afflicted subject, and consequently whether the benefits from radiotherapy will outweigh harm to the subject. Examples of genetic alterations associated with radiotherapy which are known to indicate increased sensitivity to radiation include, for example, possession of the XRCC-1 gene and increased expression of p53 protein. Possession of the XRCC-1 gene may be determined in cells, for example, by polymerase chain reaction or fluorescent in situ hybridization. Increased expression of p53 in cells may be determined, for example, by using a flow cytometric assay.

Genetic alterations associated with chemotherapy include genetic alterations associated with drug resistance. Accordingly, when a sample has been obtained from a subject who has been treated with an anti-tumor therapy which included chemotherapy, the subject method for detecting in a subject the presence of cells expressing a malignant phenotype is useful, for example, for detecting drug resistance in the subject. "Drug resistance" occurs when cells possessing a malignant phenotype remain in a subject after a regimen of chemotherapy, said cells being resistant to the therapy. Drug resistance includes multidrug resistance, which occurs when cells possessing a malignant phenotype remaining in a subject after a regimen of chemotherapy express a multidrug resistant phenotype, i.e. a phenotype associated with increased expression of mdr genes. As used herein, "a regimen of chemotherapy" includes treatment with a single chemotherapeutic agent, as well as treatment with more than one chemotherapeutic agent.

Accordingly, this invention also provides a method for determining whether a subject who has been treated with an anti-tumor therapy, said therapy having included chemotherapy, possesses cells expressing a malignant phenotype which have undergone a genetic alteration associated with drug resistance, which comprises the steps of (a) detecting in the subject the presence of cells expressing a malignant phenotype according to the method described above and; (b) determining whether any cells so detected are characteristic of cells which have undergone a genetic alteration associated with drug resistance, thereby determining whether the subject possesses cells expressing a malignant phenotype which have undergone a genetic alteration associated with drug resistance.

Genetic alterations associated with drug resistance are well-known in the art. Examples of genetic alterations associated with drug resistance include up-regulation or amplification of mdr genes, which are characteristic of multidrug resistance, or amplification of the gene encoding for dihydrofolate reductase.

Means for determining whether cells are characteristic of cells which have undergone a particular genetic alteration which is associated with drug resistance are known to those of ordinary skill in the art. For example, if the genetic alteration is amplification of mdr genes, cells having this genetic alteration may be identified by in situ hybridization with nucleic acid probes complementary to mdr genes. Amplification of mdr genes will be indicated by the quantity of probes which hybridize to the cells. If the genetic alteration is the amplification of the gene encoding for dihydrofolate reductase, cells characteristic of such a genetic alteration may be identified by in situ hybridization with a nucleic acid probe complementary to the gene encoding for dihydrofolate reductase. Amplification of the gene encoding for dihydrofolate reductase may be determined by the quantity of probe which hybridizes to the cells.

In one embodiment of the subject method for determining whether a subject who has been treated with an anti-tumor therapy having included chemotherapy possesses cells expressing a malignant phenotype which have undergone a genetic alteration associated with drug resistance, the cells expressing the malignant phenotype detected in step (a) are isolated prior to determining whether they are characteristic of cells which have undergone a genetic alteration associated with drug resistance in step (c). Any method for isolating cells may be used and will be selected based on the particular detectable ligand used in the method for detecting the cells expressing a malignant phenotype in step (a). Such methods for isolating cells are well-known to those of ordinary skill in the art as discussed above.

Once cells characteristic of a particular genetic alteration associated with drug resistance are identified, the treatment of the subject may be modified so as to destroy any remaining drug resistant cells, for example by treating the subject with a chemical against which the remaining drug resistant cells are sensitive.

This invention will be better understood from the "Experimental Details" section which follows. However, one skilled in the art will readily appreciate that the specific methods and results discussed therein are not intended to limit, and rather merely illustrate the invention as described more fully in the claims which follow thereafter.

EXPERIMENTAL DETAILS

Example 1 describes one protocol for obtaining a sample of preserved, labelled nucleated cells according to the subject invention. The rare cells preserved in Example 1 are autoreactive B lymphocytes in the peripheral blood of a lupus patient. The abbreviations used in Example 1 are FACS (fluorescence activated cell sorting), FISH (fluorescence in situ hybridization), APC (allophycocyanin), DAPI (4'6'-diamidino-2-phenyl indole), DPBS (Dulbecco's phosphate buffered saline), FCS (fetal calf serum), FITC (fluorescein isothiocyanate), HBSS (Hank's balanced salt solution), mAb (monoclonal antibody), PE (phycoerythrin), and TRITC (tetramethyl rhodamine). The antibodies used in Example 1 are commercially available and well-known to those of ordinary skill in the art.

Example 1

Preparation, Labeling and Preservation of Blood Nucleated Cells for Analysis by a Fluorescence Activated Cell Sorter Lysing Red Blood Cells 1. Pipet 5.0 ml (or less) whole peripheral blood obtained from a lupus patient into a 50 ml conical tube.

2. Dilute 10-fold with DPBS-$N_3$.Mix.

3. Centrifuge at 2,000 rpm for 10 min at 4° C.

4. Carefully aspirate supernatant.

5. Add enough lysing solution (ammonium chloride buffered with bicarbonate with no EDTA added) so that the final volume is 5-fold the starting volume of blood. Mix.

6. Incubate the cells mixed with the lysing solution on ice with further mixing for 7–10 min.

7. Add FCS so that the final concentration is 5%. Mix.

8. Centrifuge at 1,200 rpm for 5 min at 4° C. Pour off the supernatant.

9. Flick the resulting pellet to disperse cells. Wash cells twice with HBSS-N3-5%FCS.

10. Resuspend the cells with the same volume of HBSS-$N_3$-5%FCS as the starting volume of blood.

11. Remove 10 μl cells. Mix with 10 μl Trypan Blue. Count the cells in a hemacytometer.

Labeling and Preservation of Fluorophore-labeled cells for FACS

1. Pipet $10^7$ cells from the suspension obtained in step 10 into a 15 ml conical tube. Centrifuge at 1,200 rpm for 5 min at 4° C. Aspirate the supernatant.

2. Flick the resulting pellet to resuspend the cells. Add 100 μl of biotin-labeled anti-IgG and 100 μl of phycoerythrin-labeled anti-CD5 at pre-titered concentrations. Mix and incubate on ice for 20–30 min.

3. Wash the cell suspension with 10 ml HBSS-$N_3$-5%FCS.

4. Flick the pellet to resuspend the cells. Add 100 μl of FITC-labeled anti-CD20 at a pre-titered concentration, and 100 μl of APC-labeled streptavidin at 40 μg/ml. Mix and incubate on ice for 20–30 min.

5. Add 10 ml HBSS-$N_3$-5%FCS. Pellet the cells.

6. Wash the pelleted cells once with chilled DPBS-$N_3$.

7. Resuspend the pellet in 1.0 ml DPBS-$N_3$. Add 4.0 ml 3.4% formalin in DPBS-$N_3$, dropwise with mixing to the resuspension.

8. Leave in the fixative for at least 30 min.

9. Pellet the cells. Wash once with DPBS-$N_3$.

10. Store (up to 6 months) at 4° C. in the dark for FACS.

Example 2

Fluorescence In Situ Hybridization of Flow-Sorted Cells

Example 2 describes preparing mouse spleen cells, preserved as described in Example 1 and flow sorted to isolate IgE-expressing lymphocytes, for fluorescence in situ hybridization. The abbreviation used in Example 2 are the same as in Example 1. 1 XSSC is 0.015M sodium citrate plus 0.135M sodium chloride having a pH of from 7.0 to 7.4.

1. Deposit the cells onto oxysilane-coated glass slides.

2. Air-dry. Centrifuge the slides at 1,000 rpm for 10 min at room temperature.

3. Add 50 μl proteinase K in DPBS at a pre-titered concentration. Incubate the smears at 37° C. for 15 min.

4. Fix the smears with 95% ethanol at –20° C. for 15 min. Air dry.

5. Soak briefly in 2X SSC.

6. Dehydrate for 2min in 70%–85%–100% ethanol at –20° C. Air dry.

7. Warm the smears at 70°–75° C. for 5 min. Add 5–10 μl hybridization mixture, containing biotin-labeled (clone ε-6) and digoxigenin-labeled (clone μ-49) probes (11). Cover with glass cover-slips. Continue incubation for another 5 min.

8. Seal the cover-slips with rubber cement.

9. Incubate the slides at 37° C. in a moist chamber for 4–24 h.

10. Remove the seal and rinse off cover-slips in 2×SSC.

11. Wash the slides in 2×SSC-50% deionized formamide for 20 min at 43°–45° C. Wash the slides in 2×SSC for 10 min at 37°–42° C. Rinse in 4×SSC containing 0.1% Tween and 0.1% NP-40 (4×SSC-d).

12. Soak the slides in 5% non-fat dry milk (Carnation) in 4×SSC-d for 10 min at room temperature.

13. Incubate in 10 μl FITC-labeled streptavidin (Vector Labs) and TRITC-labeled anti-digoxigenin (Boehringer Mannheim) at 20 μl/ml in 4×SSC containing 5% non-fat dry milk for 20–30 min in a moist chamber at room temperature.

14. Rinse the slides twice with 4×SSC-d.

15. Incubate the slides in 5–10 μl FITC-labeled anti-streptavidin (Vector Labs) and TRITC-labeled anti-digoxigenin at 20 μl/ml.

16. Rinse the slides twice with 4×SSC-d.

17. Counterstain with DAPI at a pre-titered concentration in 1×SSC-$N_3$ for 5 min at R. T. Rinse with 1×SSC-$N_3$.

18. Mount in Elvanol. Harden overnight at 4°. Seal with varnish for long-term storage.

References

1. Adinolfi, M. 1991. Prenat. Diagn. 11:799–804.

2. Covone, A., Kozma, R., Hohnson, P. M., Latt, S. A., and Adinolfi, M. 1988. Prenat. Diagn. 8:591–607.

3. Mueller, U. W., Hawes, C. S., Wright, A. E., Petropoulos, A., DeBoni, E., Firgaira, F. A., Morley, A. A., Turner, D. R. and Jones, W. R. 1990. Lancet 336:197–200.

4. Bruch, J. F., Metezeau, P., Garcia-Fonknechten,m N., Richards, Y., Tricottet, V., Hsi, B. -L., Kitzis, A., Julien, C. and Papiernik, E. 1991. Prenat. Diagn. 11:787–798.

5. Cacheux, V., Milesi-Fluet, C., Tachdjian, G., Druart, L., Bruch, J. F., Hsi, B. L., Uzan, S. and Nessmann, C. 1992. Fetal Dign. Ther. 7:190–194.

6. Simmonds, P., Balfe, P., Peutherei, J. F., Ludlaw, C. A., Bishop, J. O., Brown, A. J. L. 1990. J. Virol. 64:864–972.

7. Patterson, B. K., Till, M., Ono, P., et al. 1993. Science 260:976–979.

8. Bagasra, O., Haupiman, S. P., Lischner, H. W., Schs, M., Pomerantz, R. J. 1992. N. Engl. J. Med. 326:1385–1391.

9. Psallidopoulos, M. C., Schninman, S. M., Thompson, L. M. III, et al. 1989. J. Virol. 63:4626–4631.

10. Mueller, U. W., Hawes, C. S., International Publication No. WO 90/06509, Jun. 14, 1990.

11. Shimizu, A., Takahashi, N., Yaoita, Y., Honjo, T., 1982. Cell. 28:499–506.

What is claimed is:

1. A method for fixing cells which comprises the steps of
   (a) suspending the cells while viable in a physiologically-acceptable, isotonic medium; and
   (b) contacting the cells so suspended with an amount of a fixative effective to fix the cells at a temperature of from about 0° C. to less than about 10° C. and under sufficiently hypertonic conditions so as to disperse the cells in a single, unagglutinated state; thereby fixing the cells.

2. A method for detecting the presence or amount of preselected cells in a sample wherein the preselected cells specifically possess on their surfaces a moiety recognized by a detectable known ligand which comprises the steps of
   (a) separating any cells in the sample;
   (b) contacting the cells so separated with the detectable known ligand under conditions which permit the detectable known ligand to specifically form a complex with the moiety recognized thereby, so as to label any cells possessing the moiety on their surfaces if present in the sample with the detectable known ligand;

(c) removing any remaining uncomplexed detectable known ligand;

(d) fixing the resulting cells according to the method of claim 1 so as to thereby fix the cells labeled in step (b); and (e) detecting the presence of the labelled cells fixed in step (d) by detecting the detectable known ligand so as to thereby detect the presence or amount of the preselected cells in the sample which specifically possess on their surfaces the moiety recognized by the detectable known ligand.

3. The method of claim 2, wherein the preselected cells are nucleated cells.

4. The method of claim 3, wherein the nucleated cells express a malignant phenotype.

5. The method of claim 3, wherein the nucleated cells are selected from the group consisting of fetal cells, tumor cells, cells infected with a virus, and cells transfected with a gene of interest.

6. The method of claim 5, wherein the nucleated cells are fetal cells.

7. The method of claim 5, wherein the nucleated cells are tumor cells.

8. The method of claim 7, wherein the tumor cells are from a tumor selected from the group consisting of a melanoma, a breast tumor, a spleen tumor, a liver tumor, and a kidney tumor.

9. The method of claim 2, wherein the sample includes erythrocytes and the erythrocytes are removed from the sample prior to step (d).

10. The method of claim 2, wherein the moiety is a receptor.

11. The method of claim 2, wherein the moiety is an epitope and the detectable known ligand is an antibody which binds to the epitope.

12. The method of claim 2, farther comprising quantitatively determining the amount of the cells in step (e).

13. A method for isolating preselected cells in a sample which cells specifically possess on their surfaces a moiety recognized by a detectable known ligand which comprises the steps of (a) separating any cells in the sample;

(b) contacting the cells so separated with the detectable known ligand under conditions which permit the detectable known ligand to specifically form a complex with the moiety recognized thereby, so as to label any cells possessing the moiety on their surfaces if present in the sample with the detectable known ligand;

(c) removing any remaining uncomplexed detectable known ligand;

(d) fixing the resulting cells according to the method of claim 1 so as to thereby fix the cells labeled in step (b);

(e) detecting the presence of the labelled cells fixed in step (d) by detecting the detectable known ligand; and (f) isolating the detected cells detected m step (e), so as to thereby isolate the preselected cells in the sample which specifically possess on their surfaces the moiety recognized by the detectable known ligand.

* * * * *